United States Patent [19]

Pachter et al.

[11] 3,966,940

[45] June 29, 1976

[54] ANALGETIC COMPOSITIONS

[75] Inventors: Irwin J. Pachter, Fayetteville; Maxwell Gordon, Syracuse, both of N.Y.

[73] Assignee: Bristol-Myers Company, New York, N.Y.

[22] Filed: Sept. 2, 1975

[21] Appl. No.: 609,847

Related U.S. Application Data

[63] Continuation of Ser. No. 414,567, Nov. 9, 1973, abandoned, which is a continuation-in-part of Ser. No. 60,621, Aug. 3, 1970, Pat. No. 3,773,955.

[52] U.S. Cl. .................................. 424/260; 424/10; 424/330

[51] Int. Cl.[2] ....................................... A61K 31/485

[58] Field of Search ....................... 424/260, 10, 330

[56] References Cited

UNITED STATES PATENTS

| | | | |
|---|---|---|---|
| 2,770,569 | 11/1956 | Fromherz et al. | 424/260 |
| 3,254,088 | 5/1966 | Lewenstein et al. | 424/260 |
| 3,466,277 | 9/1969 | Merz et al. | 424/260 |
| 3,493,657 | 2/1970 | Lewenstein et al. | 424/260 |

FOREIGN PATENTS OR APPLICATIONS

| | | | |
|---|---|---|---|
| 751,767 | 7/1956 | United Kingdom | 424/260 |
| 769,517 | 3/1957 | United Kingdom | 424/260 |
| 831,873 | 4/1960 | United Kingdom | 424/260 |
| 791,644 | 3/1958 | United Kingdom | 424/10 |
| 808,269 | 1/1959 | United Kingdom | 424/10 |

OTHER PUBLICATIONS

Goodman et al., Pharm. Basis of Therapeutics, 3rd Edition, (1965), pp. 274–279.

Merck Index 8th Edition, 1968 p. 371.

*Primary Examiner*—Norman A. Drezin
*Attorney, Agent, or Firm*—Robert E. Havranek

[57] ABSTRACT

Orally effective, analgetic compositions have been developed which are useful in the prevention of drug abuse because upon parenteral administration, they do not produce analgesia, euphoria, or physical dependence. Such compositions comprise an orally active, strong analgetic in oral dosage form and containing, for each analgetic dose of the analgetic agent, an amount of naloxone sufficient, upon parenteral administration of said oral dosage form, to negate the analgetic, euphoretic and dependence producing action of the composition, but insufficient to block the therapeutic effect of the analgetic when the admixture is taken orally.

4 Claims, No Drawings

ANALGETIC COMPOSITIONS

CROSS REFERENCE TO RELATED APPLICATIONS

This application is a continuation of application Ser. No. 414,567, filed Nov. 9, 1973, now abandoned, which application was a continuation-in-part of application Ser. No. 60,621, filed Aug. 3, 1970, now U.S. Pat. No. 3,773,955.

BACKGROUND OF THE INVENTION

1. Field of the Invention

This invention is in the field of combinations of drugs for medicinal purposes, in particular, analgetic compositions for the treatment of pain and is more particularly concerned with the prevention of a particular type of drug abuse, i.e., the illicit use by parenteral administration of dosage forms intended for oral administration.

2. Description of the Prior Art

A. U.S. Pat. No. 3,254,088, which issued May 31, 1966, describes the preparation of naloxone and its activity as a narcotic antagonist.

B. U.S. Pat. No. 3,493,657, which issued Feb. 3, 1970, describes the combination of morphine and naloxone as a composition for parenteral use "which has a strong analgetic, as well as antagonistic effect, without the occurrence of undesired or dangerous side effects."

C. A New York Times article appearing in a July 14, 1970 issue describes the oral administration of naloxone to narcotic addicts as a method of treatment. The oral administration of naloxone (in high doses) "makes it impossible for the addict to experience a high no matter how much heroin he uses."

Applicants are of the opinion that the prior art neither teaches nor suggests that compositions of the instant invention can be effectively employed to overcome the problem of parenteral abuse of oral dosage formulations without diminishing or suppressing oral efficacy because such compositions are orally active as analgetic agents, but produce neither analgesia, euphoria, or physical dependence when administered parenterally.

Drug abuse has almost become a way of life to a rapidly growing segment of the world population, especially here in the United States. It has become the vogue of many of the younger generation to experiment with any type of drug that will produce an emotional, psychological, euphoric, depressive or generally psychodelic experience.

Those drugs most commonly employed for such illicit purposes include the barbiturates, lysergic acid diethylamide (LSD), mescaline, marijuana (tetrahydrocannabinol), strong analgetics (heroin, codeine, morphine, meperidine, propoxyphene [Darvon], methadone, dihydrocodeinone, pentazocine, and the like), the central nervous system stimulants (the amphetamines and the like) and some of the major and minor tranquilizers (the promazines, meprobamate, the diazepines, and the like). Most of these compounds are commonly used in medicine for the legitimate treatment of various conditions and therefore have a limited availability in our society. While these agents are a necessary part of modern medicine, it would be highly desirable (1) to produce new drugs that do not possess drug abuse potential or (2) to "denature" the old agents to prevent their illicit use. The pharmaceutical industry has been striving to achieve the first goal for many years but most regretably has only achieved very moderate success. If one focuses on the strong analgetics, it becomes apparent that much effort and money has been expended to produce chemicals possessing good analgetic activity but little or no addictive liability. While good progress has been made as evidenced, for example, by the development of propoxyphene as a replacement for codeine and pentazocine as a replacement for morphine or meperidine, it is unfortunate that these compounds are still reported in the medical literature to be addictive and/or euphoric and subjected to abuse by parenteral administration. Furthermore, some of these agents have undesirable side effects, i.e., bad hallucinations, etc.

It is commonly known to the narcotic enforcement agencies and others in the medical trades that a substantial amount of the strong analgetics destined for legitimate medicinal use are diverted to illicit use through dishonest or careless handling. In many instances, these drugs are obtained by the addict or potential addict by theft or casual prescribing practice by the physician.

It is known from experience that the true narcotic addict must feed his habit by the parenteral route (mainlining) to obtain the maximum euphoric effect. The potential addict or thrill-seeker will also experiment in the same manner. Unfortunately, a substantial amount of the legitimate strong analgetics formulated in oral dosage form are diverted to illicit parenteral use, i.e., the type of abuse with which this invention is concerned. Since the oral dosage forms of these drugs diverted from legitimate channels must be parenterally effective to produce the desired euphoria, it follows that if these oral dosage forms are in some way rendered inactive or unpleasant for parenteral use the addict or potential addict will be cut off from this particular supply of euphoretic drugs. Obviously, oral activity must be retained if a useful medicament is to be provided.

Naloxone, chemically known as 1-N-allyl-14-hydroxynordihydromorphinone (Merck Index, 8th Ed., p. 712, Merck and Co., Rahway, New Jersey; U.S. Pat. No. 3,254,088 [1966], is a potent narcotic antagonist when administered parenterally. This compound is useful for the treatment of narcotic overdosage or for the detection of addiction. However, while naloxone is extremely potent parenterally (a parenteral dose of 0.1 mg. to 2.5 mg. will produce narcotic withdrawal symptoms in the addict or have a narcotic reversal effect in an overdose situation), the compound must be administered orally in quantities 200 to 400 times greater to produce an equivalent effect. It is known that the contemporaneous parenteral administration of equivalent therapeutic doses of naloxone and an euphoretic narcotic or narcotic-like analgetic will negate the analgetic and euphoretic effect in the normal individual and the euphoric and/or maintenance effect of the analgetic in the addict.

Many interchangeable terms are commonly used to describe the psychic or physical dependence of people upon drugs. The term addiction is most commonly used when talking about the strong analgetics. The strong analgetics, in contrast to the weaker agents such as aspirin, acetaminophen, and the like, are employed in the relief of more severe pain. They usually produce a euphoric effect when taken parenterally. Orally there is usually no significant euphoria.

Addiction can develop to the barbiturates and strong analgetic agents, in the sense of the term "addiction" as defined by the Committee on Problems of Drug Dependence of The National Research Council, namely, a state of periodic or chronic intoxication, detrimental to the individual and to society, produced by the repeated administration of a drug, its characteristics are a compulsion to take the drug and to increase the dose, with the development of psychic and sometimes physical dependence on the effects of the drug, so that the development of means to continue the administration of the drug becomes an important motive in the addict's existence.

Addiction to narcotics or narcotic-like strong analgetics often occurs by the legitimate chronic parenteral administration of these agents in the alleviation of deep pain. More commonly, however, addiction to these agents occurs when the psychologically unbalanced or thrill-seeking individual looking for an escape from the realities of life finds his escape in the euphoria produced by the parenteral administration of strong analgetics. Euphoria is generally defined as a feeling of well-being. Euphoria can be produced in many ways, e.g., an exhilerating experience, alcohol, stimulants, depressants, narcotics, etc. For the purpose of this disclosure, "euphoria" is defined as an abnormal state of well-being produced by the parenteral administration of strong analgetics. The terms "euphoretic analgetics" and "strong analgetics," often called narcotic or narcotic-like analgetics, are also defined herein as including those chemical agents which upon parenteral administration are capable of maintaining or partially maintaining a known addict addicted to heroin or the like without substantial withdrawal symptoms. For the purpose of this disclosure, a "strong analgetic" can also be described as any analgetic agent whose analgetic, euphoric or dependence producing actions are negated by the parenteral administration of naloxone or a salt thereof.

SUMMARY OF THE INVENTION

This invention is concerned with the development of a potent, orally effective, but parenterally inactive analgetic composition that has substantially reduced drug abuse potential and, more particularly, essentially no abuse potential due to parenteral abuse. The objects of the invention are achieved by the formulation of a composition comprising an orally active strong, i.e., narcotic or narcotic-like, analgetic agent in oral dosage form and naloxone in an amount which is insufficient to diminish the therapeutic effect of the narcotic upon oral administration but which at the same time completely negates all the characteristic narcotic properties of the narcotic if taken parenterally.

Another aspect of the invention is to provide a means for selective denaturation of a strong analgetic or narcotic formulation. The term "selective denaturation," as used herein, refers to the elimination of certain inherent properties of a narcotic compound when given by a particular route of administration. When such terminology is used, we refer to a narcotic composition which has all the inherent characteristics of a narcotic when given orally, but which has none of these properties when taken parenterally. "Selectively denaturing" or "selectively denatured" are used herein to describe compositions in which the amount of naloxone is effective to substantially suppress the parenteral effect of the narcotic agent. Similarly, the term "selectively denatured amount" refers to an amount of naloxone sufficient to substantially suppress the euphoretic, analgetic, and dependence inducing effect of the oral narcotic composition when taken parenterally. It will be appreciated that the actual amount of naloxone which constitutes a selectively denaturing amount will vary depending on the nature of the narcotic and its effective oral and parenteral dosages.

Another objective achieved by this invention is the provision of a means for preventing abuse of oral formulations of therapeutically valuable strong analgetics by the improvement in formulating such medicaments which comprises admixing therewith a balanced amount of naloxone, i.e., an amount of naloxone which is orally less than will block the therapeutic effect of the analgetic but is at the same time sufficient to completely block all the expected effects of the analgetic if taken parenterally.

It is our invention to combine a parenterally effective but orally ineffective dose of naloxone with an oral analgetic dose of an orally effective strong analgetic, thereby to render the analgetic ineffective but only on parenteral administration. There is no less in the therapeutic effect of the analgetic when taken by the intended route. At the same time, however, if any of the oral dosage form should be diverted to illicit use, it would not produce any euphoria and in an addict would, in fact, induce withdrawal symptoms.

Examples of some representative orally active strong analgetics which are within the contemplation of the invention and their preferred oral dosage ranges include: meperidine (50-250 mg.), oxymorphone (5-25 mg.), alphaprodine (50-250 mg.), anileridine (25-150 mg.), dextromoramide (5-25 mg.), dextroporpoxyphene (32-150 mg.), methadone (5-25 mg.), metopon (3-15 mg.), levorphanol (2-10 mg.), phenazocine (2-10 mg.), etoheptazine (100-500 mg.), propiram (50-500 mg.), profadol (20-250 mg.), phenampromide (50-250 mg.), thiambutene (20-150 mg.), pentazocine (20-200 mg.), pholcodeine (25-250 mg.), codeine (15-150 mg.), oxycodone (5-50 mg.), dihydrocodeinone (5-100 mg.), hydromorphone (10-100 mg.), fentanyl (0.5-10 mg.), 3-trans-dimethylamino-4-phenyl-4-trans-carbethoxy-Δ'-cyclohexene (50-250 mg.), 3-dimethylamino-0-(4-methoxyphenylcarbamoyl)-propiophenone oxime ( 25-150 mg.), (−)β-2'-hydroxy-2,9-dimethyl-5-phenyl-6,7-benzomorphan (10-150 mg.), (−)2'-hydroxy-2-(3-methyl-2-butenyl)-9-methyl-5-phenyl-6,7-benzomorphan (20-300 mg.), pirinitramide (10-150 mg.), (−)α-5,9-diethyl-2'-hydroxy-2-methyl-6,7-benzomorphan (50-250 mg.), ethyl 1-(2-dimethylaminoethyl)-4,5,6,7-tetrahydro-3-methyl-4-oxo-6-phenylindole-2-carboxylate (50-150 mg.), 1-Benzoylmethyl-2,3-dimethyl-3-(m-hydroxyphenyl)-piperidine (50-500 mg.), N-allyl-7α-(1-(R)-hydroxy-1-methylbutyl)-6,14-endo-ethanotetrahydronororipavine (50-250 mg.), (−)2'-hydroxy-2-methyl-6,7-benzomorphan (50-250 mg.), noracylmethadol (10-150 mg.), phenoperidine (5-100 mg.), α-dl-methadol (5-25 mg.), β-dl-methadol (35-250 mg.), α-1-methadol (2-15 mg.), β-dl-acetylmethadol (1-10 mg.), α-1-acetylmethadol (1-10 mg.) and β-1-acetylmethadol (2-25 mg.).

When the term naloxone or the name of a strong analgetic agent is used herein, it is to be understood that any and all the pharmaceutically acceptable nontoxic salts thereof are also an integral part of this invention. The salts of these agents would include the hydrochlorides, sulfates, bisulfates, tartrates, nitrates, citrates, bitartrates, phosphates, malates, maleates, hydrobromides, hydroiodides, fumarates, succinates, and the like.

The compositions of the present invention can be formulated into any of the known pharmaceutical forms for oral administration. As such, the term "oral dosage form" includes solid compositions for oral administration in unit dosage form such as tablets, capsules, granules, powders, cachets or the like. Bulk powders of fixed composition for subdivision into therapeutic quantities, solutions, emulsions or suspensions of the composition are also included in the definition.

The compositions of the instant invention can also contain other active ingredients. These include amongst others for example, aspirin, phenacetin, caffeine, acetaminophen, antihistamines, homatropine methylbromide, phenyltoloxamine citrate, barbiturates, or the like, or multiple combinations thereof. Also included within the scope of the present invention are those compositions comprising naloxone in combination with those antitussive preparations which contain narcotic or narcotic-like cough suppressants such as codeine, dihyrocodeinone, pholcodeine, and the like. Other products comprising a narcotic or narcotic-like composition for use as an antispasmotic in the gastro-intestinal tract, such as Camphorated Opium Tincture, U.S.P., Opium Tincture, U.S.P., Opium extract, N.F., and the like can also be denatured with naloxone and are to be considered an integral part of this invention.

One especially valued aspect of the present invention is the use of certain strong analgetics in combination with naloxone in the treatment of drug addicts. Methadone maintenance is one of the methods of treating narcotic addicts. The regimen of treatment involves the oral dosing of the addict one or more times a day with a maintenance dose of methadone adequate to prevent narcotic craving. When taken orally, the methadone dose does not cause euphoria. One problem of the program is the necessity for the former addict to report to a treatment center one or more times a day to receive his methadone. The oral methadone must be administered in the presence of a health officer to prevent its diversion to illicit channels where it can be abused parenterally so as to obtain a euphoric effect. However, this would not be so if the composition of the instant invention were to be employed. As explained above, the naloxone-methadone composition as disclosed herein would be orally active but could not be diverted to parenteral use because of the presence of the naloxone. It would, therefore, be possible to supply an addict with several days supply of his maintenance dose of methadone without fear of the composition being used for other than that intended. Certain methadone analogues such as $\alpha$-dl-methadol, $\beta$-dl-methadol, $\alpha$-1-methadol and the acetylmethadols are also of interest in the treatment of addicts and, in combination with naloxone, are suitable for the formulation of parenterally denatured oral dose formulations. These formulations are also very useful as analgetics for the alleviation of pain in non-addict subjects.

A preferred embodiment of the present invention is an orally effective, analgetic composition which, upon parenteral administration does not produce analgesia, euphoria or physical dependence, said composition comprising an orally ineffective but parenterally effective dose of naloxone and an analgetic dose of an orally active, strong analgetic in oral dosage form. Such a composition can be further described as containing for each analgetic dose of the analgetic agent an amount of naloxone sufficient upon parenteral administration of said oral dosage form to negate the analgetic and euphoric action of the composition.

In formulating such compositions, one part by weight of naloxone can be admixed with 40 to 400 parts of meperidine, 0.4 to 4 parts of oxymorphone, 13 to 130 parts of alphaprodine, 12 to 120 parts of anileridine, 2 to 20 parts of dextromoramide, 12 to 120 parts of dextropropoxyphene, 2.5 to 25 parts of methadone, 0.3 to 3 parts of metopon, 0.8 to 8 parts of levorphanol, 0.8 to 8 parts of phenazocine, 60 to 600 parts of etoheptazine 20 to 200 parts of propiram, 8 to 80 parts of profadol, 40 to 400 parts of phenampromide, 10 to 100 parts of thiambutene, 8 to 80 parts of pentazocine, 4 to 40 parts of pholcodeine, 15 to 150 parts of codeine, 2 to 20 parts of oxycodone, 2.5 to 25 parts of dihydrocodeinone, 0.8 to 8 parts of hydromorphone, 0.1 to 1 part fentanyl, 15 to 150 parts of 3-trans-dimethylamino-4-phenyl-4-trans-carbethoxy-$\Delta'$-cyclohexene, 6 to 60 parts of 3-dimethylamino-0-(4-methoxyphenylcarbamoyl)-propiophenone oxime, 5 to 50 parts of $(-)\beta$-2'-hydroxy-2,9-dimethyl-5-phenyl-6,7-benzomorphan, 13 to 130 parts of (−)2'-hydroxy-2-(3-methyl-2-butenyl)-9-methyl-5-phenyl-6,7-benzomorphan, 5 to 50 parts of pirinitramide, 5 to 50 parts of $(-)\alpha$-5,9-diethyl-2'-hydroxy-2-methyl-6,7-benzomorphan, 5 to 50 parts of ethyl 1-(2-dimethylaminoethyl)-4,5,6,7-tetrahydro-3-methyl-4-oxo-6-phenyl-indole-2-carboxylate, 20 to 200 parts of 1-Benzoylmethyl-2,3-dimethyl-3-(m-hydroxyphenyl)-piperidine, 0.1 to 1 part N-allyl-7$\alpha$-(1-(R)-hydroxy-1-methylbutyl)-6,14-endoethenotetrahydronororipavine, 14 to 140 parts of (−)2'-hydroxy-2-methyl-6,7-benzomorphan, 5 to 50 parts of noracylmethadol, 2 to 20 parts of phenoperidine, 2.5 to 25 parts of $\alpha$-dl-methadol, 40 to 400 parts of $\beta$-dl-methadol, 0.3 to 3 parts of $\alpha$-1-methadol, 0.8 to 8 parts of $\beta$-dl-acetylmethadol, 0.8 to 8 parts of $\alpha$-1-acetylmethadol or 0.4 to 4 parts of $\beta$-1-acetylmethadol, in oral dosage form.

In general, compositions of the present invention can contain from about 0.1 mg. to about 10 mg. of naloxone per analgetic oral dose of a herein disclosed orally active, strong analgetic in oral dosage form.

Another aspect of the present invention is the method of producing analgesia in mammals by the oral administration of an orally effective, analgetic composition which, upon parenteral administration, does not produce analgesia, euphoria, or physical dependence, said composition comprising an orally ineffective but parenterally effective dose of naloxone and an orally active, strong analgetic in oral dosage form.

The compositions of this invention are useful as oral analgetics and therefore are useful in the method of producing analgesia in man which comprises the oral administration of an orally effective analgetic composition which, upon parenteral administration, does not produce analgesia, euphoria or physical dependence, said composition comprising about 0.1 to about 2.5 mg. of naloxone per analgetic oral dose of an orally active, strong analgetic in oral unit dosage form.

It will be appreciated that this invention can be variously described, e.g., as a means of preventing abuse by route of administration, or as an improvement in the formulation and compounding of oral strong analgetic compositions. However, all based on the discovery that unique combinations of characteristics of various analgetics and the narcotic antagonist naloxone can be utilized to provide valuable medicaments substantially free of any potential for illicit use specifically by administration via a means other than the intended oral route.

The weight ratios of naloxone to the analgetic agents in the composition of the instant invention disclosed herein have been determined either from the literature or in our laboratories. It has been found that the parenteral administration of one part by weight of naloxone will efficiently and reliably negate (counteract) the parenteral effect of the most usually employed oral dose of the narcotic as described above.

It has also been established that naloxone can be administered orally in a quantity up to about ten times the minimal parenteral dose required to abolish parenteral activity of the analgetic without abolishing the oral activity of the analgetic, e.g., 1 part naloxone per 40 parts meperidine, 1 part naloxone per 0.8 parts phenazocine, etc.

Working from these parenteral ratios which define the minimum efficient and reliable parenteral dose of naloxone required to negate the euphoretic and other effects of the parenteral dose of the analgetic agent, other experiments have been conducted to determine the largest practical and economical quantity of naloxone that can be administered orally in combination with an oral therapeutic dose of the analgetic agent without abolishing the therapeutic effect of the analgetic agent. It was found that one can safely administer naloxone orally in a quantity up to about ten times the minimal parenteral dose necessry to abolish parenteral activity of the orally effective dose of the analgetic. It is emphasized here that it is frequently possible to orally administer more than ten times the minimum parenteral dose of the naloxone without abolishing the oral analgetic effect.

The "rat tail-flick" method was used in our laboratory to determine the naloxone analgetic ratios of some of the euphoretic analgetic agents. The method adopted for use is that originally described by D'Amour and Smith (J. Pharmacol. Exper. Therap. 72:74, 1941) in which a heat lamp is focused onto a rat's tail and the elapsed time between onset of the light and a flick of the tail is measured. The method consists of holding the animal either by wrapping it in a towel or box with the tail laying in a V-shaped groove. The light and timer are connected in series with a switch so that both the light and timer can be turned on and off simultaneously. When the rat quiets down, the light and timer are turned on and the operator watches for the response, which is a characteristic flick of the tail. The response, in the control period for the untreated rat is usually about 3.5 seconds. Rats weighing between 160 to 190 grams have been found most uniform in response in the control and treated trials.

An example of one experiment is the determination of the parenteral ratio for oxymorphone in rats.

Untreated rats produced the desired "tail-flick" in 3.5 seconds. A differing amount of oxymorphone hydrochloride was administered subcutaneously to a sequence of rats to determine the minimum quantity of oxymorphone hydrochloride necessary to delay the "tail-flick" till 7 seconds. The amount required was 0.22 mg./kg. body weight.

A series of rats so treated with oxymorphone hydrochloride were then challenged with varying doses of subcutaneously administered naloxone hydrochloride to determine the minimum quantity of naloxone that would completely negate the analgesia produced by the oxymorphone. The quantity required was 0.025 mg./kg. body weight. The parenteral naloxone/analgetic ratio is therefore approximately 1 part naloxone hydrochloride to about 9 parts of oxymorphone hydrochloride.

Once it was established that the parenteral administration of 1 part of naloxone would completely negate the analgetic activity of about 9 parts of oxymorphone, it was necessary to determine how the ratio would work when the combination was administered orally.

A series of starved rats were orally dosed by stomach tube with varying quantities of oxymorphone necessary to produce a "tail-flick" response of 7 seconds. The dose of oxymorphone hydrochloride was dissolved in 20 ml. of water per kg. of body weight. It was determined that 50 mg./kg. orally produced the desired "tail-flick" response in 6 of 6 rats. A dose of 25 mg./kg. produced the desired response in 5 of 6 rats.

A composition of 1.1 grams of naloxone hydrochloride and oxymorphone hydrochloride was prepared containing 0.1 gram of naloxone HCl and 1.0 gram of oxymorphone HCl (1:10 ratio).

A dose of 27.5 mg./kg. of body weight of the above composition dissolved in 20 ml. of water was administered by stomach tube. Six of 6 rats showed a "tail-flick" response of at least 7 seconds. When a dose of 55 mg./kg. was administered, 6 of 6 rats again showed the desired analgetic effect of at least 7 seconds.

In a similar experiment to that described above, it was determined that 50 mg./kg. of phenazocine orally produced the desired "tail-flick" response in 5 of 6 rats. A dose of 100 mg./kg. produced the desired response in 6 of 6 rats.

A composition of 0.64 gm. of naloxone hydrochloride and phenazocine hydrobromide was prepared containing 0.04 gm. of naloxone HCl and 0.60 gm. of phenazocine HBr (1:15 ratio).

A dose of 53.3 gm./kg. of body weight of the above composition dissolved in 20 ml. of water was administered by stomach tube. Six of 6 rats showed a "tail-flick" response of at least 7 seconds. When a dose of 106.6 mg./kg. was administered, 6 of 6 rats again showed the desired analgetic effect of at least 7 seconds.

In further experiments with phenazocine HBr, it was found that compositions containing doses of naloxone in 100% excess of the minimal antagonistic parenteral dose still produced analgesia upon oral administration.

The conclusion can therefore be drawn that a parenterally antagonistic dose of naloxone can be adninistered orally without interfering with the analgetic effect of the orally administered analgetic.

Applicants acknowledge the possibility of different naloxone/analgetic ratios due to species difference, e.g., rat versus man, etc. For example, our laboratory studies show 1 part of parenterally administered naloxone hydrochloride will negate the analgetic effect of about 9 parts of parenterally administered oxymorphone hydrochloride in the rat. However, it is reported in the literature that 1 part of naloxone HCl parenterally is required to negate the analgetic effect of 4 parts of oxymorphone HCl parenterally in man.

Likewise, it was found that 1 part of naloxone parenterally would negate the effect of about 15 parts of phenazocine HBr in the rat, but the literature reports that 1 part of naloxone parenterally is required to negate the effect of 8 parts of phenazocine HBr parenterally in man.

By balancing the relative proportions of strong analgetic and naloxone, it has been found possible to achieve a selective denaturation of the narcotic characteristics, depending upon the route of administration, thereby making it possible to combine in a single therapeutic dosage form the characteristics of a useful medicament and a strong deterrent to the most serious form of abuse to which the therapeutic dosage form is subject. Since the ratio of ingredients is dependent on the physiological activity of the strong analgetic, the relative amounts of naloxone and strong analgetic agent will be different for each analgesic. The selection of ratios is very important because of diverse physiological effects. For example, the amount of naloxone must not interfere with the normal therapeutic or analgesic activity of the pain-relieving drug, while at the same time be sufficient to overcome or antagonize the euphoria which is expected to be caused by parenteral assimilation. As an additional factor, one does not want to cause severe abstinence symptoms in any addict foolish enough to divert the oral medication to illicit use. Accordingly, the oral versus parenteral activities of both naloxone and the selected analgetic must be balanced with respect to both length of action and the rapidity of onset.

| Description of Some Specific Compositions | |
|---|---|
| Example 1 | |
| Naloxone Hydrochloride | 0.10 gram |
| Methadone Hydrochloride | 0.500 gram |
| Lactose qs. ad. | 100 capsules |
| Example 2 | |
| Naloxone Hydrochloride | 1.0 gram |
| Phenazocine Hydrobromide | 2.5 grams |
| Magnesium Stearate qs. | |
| Corn Starch qs. ad. | 1000 tablets |
| Example 3 | |
| Naloxone Hydrochloride | 0.050 gram |
| Meperidine Hydrochloride | 5.0 grams |
| Corn Starch | |
| Talc āā qs. ad. | 100 capsules |
| Example 4 | |
| Naloxone Hydrochloride | 0.5 gram |
| Methadone Hydrochloride | 5.0 grams |
| Lactose qs. ad. | 100 capsules |
| Example 5 | |
| Naloxone Hydrochloride | 0.4 gram |
| Codeine Sulfate | 30 grams |
| Magnesium Stearate qs. | |
| Corn Starch qs. ad. | 1000 tablets |
| Example 6 | |
| Naloxone Hydrochloride | 1.0 gram |
| Dextropropoxyphene Hydrochloride | 65.0 grams |
| Lactose qs. ad. | 1000 capsules |
| Example 7 | |
| Naloxone (or a salt thereof) | .050 gram |
| Camphorated Opium Tincture, U.S.P., qs. ad. | 100 ml. |

We claim:

1. A method for the treatment of a narcotic-addicted subject which comprises orally administering to said subject an effective amount of a composition consisting essentially of (a) a narcotic selected from the group consisting of α-dl-methadol, β-dl-methadol, α-1-methadol, β-dl-acetylmethadol, α-1-acetylmethadol and β-1-acetylmethadol in an amount sufficient to substantially prevent narcotic craving and (b) naloxone in an amount sufficient to induce withdrawal symptoms when said composition is administered parenterally but insufficient to negate the action of said methadone when the composition is administered orally.

2. The method of claim 1 wherein said narcotic is α-1-acetylmethadol.

3. The method of claim 2 wherein the weight ratio of α-1-acetylmethadol to naloxone is from about 2.5:1 to about 25:1.

4. The method of claim 2 wherein said composition comprises from about 0.1 to about 10 milligrams of naloxone per analgetic oral dose of α-1-acetylmethadol.

* * * * *